United States Patent [19]

Kerber

[11] Patent Number: 5,529,974
[45] Date of Patent: Jun. 25, 1996

[54] SELECTIVE SAFENED HERBICIDAL COMPOSITION

[75] Inventor: Elmar Kerber, Görwihl, Germany

[73] Assignee: Ciba-Geigy Corporation, Tarrytown, N.Y.

[21] Appl. No.: 462,446

[22] Filed: Jun. 5, 1995

Related U.S. Application Data

[63] Continuation of Ser. No. 389,435, Feb. 15, 1995, abandoned, which is a continuation of Ser. No. 149,413, Nov. 9, 1993, abandoned.

[30] Foreign Application Priority Data

Nov. 12, 1993 [CH] Switzerland .................. 3493/92

[51] Int. Cl.$^6$ ........................................ A01N 25/32
[52] U.S. Cl. ........................................ 504/112
[58] Field of Search ............... 504/112; A01N 25/32

[56] References Cited

U.S. PATENT DOCUMENTS

| | | | |
|---|---|---|---|
| 4,579,583 | 4/1986 | Föry et al. | 71/92 |
| 4,690,707 | 9/1987 | Föry et al. | 71/93 |
| 5,215,570 | 6/1993 | Burckhardt et al. | 504/112 |
| 5,221,315 | 6/1993 | Föry et al. | 504/178 |

FOREIGN PATENT DOCUMENTS

| | | |
|---|---|---|
| 314505 | 10/1988 | European Pat. Off. . |
| 365484 | 4/1990 | European Pat. Off. . |
| 0492367 | 7/1992 | European Pat. Off. . |
| 4000503 | 7/1991 | Germany . |
| 9317016 | 9/1993 | WIPO . |

OTHER PUBLICATIONS

Chem. Abst. 116: 174163j of DE 4,000,503 1992.
Chem. Abst. 117:126460c; Klaus, et al. (1992).

*Primary Examiner*—S. Mark Clardy
*Attorney, Agent, or Firm*—George Dohmann; Marla J. Mathias; William A. Teoli, Jr.

[57] ABSTRACT

Mixtures comprising a herbicidally effective amount of a pyridylsulfonylurea of formula I

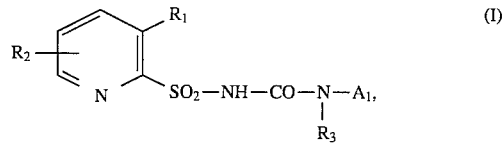

wherein $R_1$, $R_2$, $R_3$ and A are as defined in claim 1, and a herbicide-antagonistically effective amount of a sulfamoylphenylurea of formula II

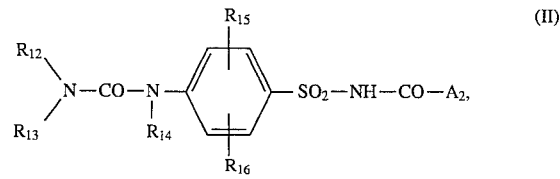

wherein $R_{12}$ to $R_{16}$ and $A_2$ are as defined in claim 1, are very suitable for the control of weeds in crops of useful plants, especially maize.

7 Claims, No Drawings

SELECTIVE SAFENED HERBICIDAL COMPOSITION

This application is a continuation of Ser. No. 08/389,435, filed Feb. 15, 1995, now abandoned, which is a continuation of Ser. No. 08/149,413, filed Nov. 9, 1993, now abandoned.

The present invention relates to a selective herbicidal composition for controlling grasses and weeds in crops of useful plants, especially in maize crops, comprising a herbicide and a safener (antidote) which protects the useful plants, but not the weeds, from the phytotoxic action of the herbicide, and to the use of that composition or of the combination of herbicide and safener in the control of weeds in crops of useful plants.

When herbicides are used, considerable damage may be caused to the crop plants depending on such factors as the concentration of the herbicide and the mode of application, the species of crop plant, the nature of the soil and climatic conditions, for example period of exposure to light, temperature and rainfall. In particular, severe damage can be caused if, in the course of crop rotation, crop plants that are resistant to the herbicides are followed by other crop plants that have no or only insufficient resistance towards the herbicides.

In order to counter that problem, various compounds have already been proposed that are capable of specifically antagonising the damaging effect of the herbicide on the crop plant, that is to say of protecting the crop plant without at the same time significantly affecting the herbicidal action against the weeds to be controlled. It has been found that the proposed safeners are often very species- or type-specific both as regards the crop plants and as regards the herbicide and in some cases also as a function of the mode of application, that is to say a specific safener is often suitable only for a specific crop plant and a specific class of herbicidal compound.

It has now been found that sulfamoylphenylureas known from EP-A-0 365 484 are suitable for protecting crop plants from the phytotoxic action of a specific class of pyridylsulfonylurea herbicides.

There is therefore proposed according to the invention a selective herbicidal composition that comprises as active component, in addition to inert carriers and additives, a mixture comprising a) a herbicidally effective amount of a pyridylsulfonylurea of formula I $$R_2 \underset{N}{\overset{R_1}{\diagdown}} SO_2-NH-CO-N-A_1, \quad (I)$$
$$\qquad\qquad\qquad\qquad\quad |$$
$$\qquad\qquad\qquad\qquad\quad R_3$$

wherein $R_1$ is $Si(CH_3)_3$, $-OSO_2NR_4R_5$, $-NR_6R_7$ or iodine, $R_2$ is hydrogen, $C_1-C_3$alkyl, $C_1-C_3$haloalkyl, halogen, $NO_2$, $CN$, $C_1-C_3$alkoxy, $C_1-C_3$haloalkoxy, $C_1-C_3$alkylthio, $C_1-C_3$alkoxy-$C_1-C_3$alkyl, $C_1-C_3$alkoxycarbonyl, $C_1-C_3$alkylamino, di($C_1-C_3$alkyl)amino, $C_1-C_3$alkylsulfinyl, $C_1-C_3$alkylsulfonyl, $SO_2NR_8R_9$ or $C(O)NR_8R_9$, $R_8$ and $R_9$ are each independently of the other hydrogen, $C_1-C_3$alkyl, $C_3$- or $C_4$-alkenyl or propargyl, or together are $-(CH_2)_4-$, $-(CH_2)_5-$ or $-CH_2CH_2OCH_2CH_2-$, $R_3$ is hydrogen or $CH_3$, $R_4$ is hydrogen, $C_1-C_3$alkyl, $C_3-C_4$alkenyl, $C_1-C_3$alkoxy or propargyl and $R_5$ is hydrogen, $C_1-C_3$alkyl, $C_3-C_4$alkenyl or propargyl, or $R_4$ and $R_5$ together are $-(CH_2)_4-$, $-(CH_2)_5-$ or $-CH_2CH_2OCH_2CH_2-$, $R_6$ is hydrogen, $C_1-C_4$alkyl, $C_1-C_4$alkylsulfonyl or phenylsulfonyl wherein the phenyl group may be substituted by halogen, $C_1-C_4$alkyl and/or by $C_1-C_4$alkoxy; $C_3$- or $C_4$-alkenyl or $C_3$- or $C_4$-alkynyl, $R_7$ is $C_1-C_4$alkylsulfonyl or phenylsulfonyl wherein the phenyl group may be substituted by halogen, $C_1-C_4$alkyl and/or by $C_1-C_4$alkoxy, $A_1$ is a group of the formula

[chemical structures]

X is hydrogen, halogen, $C_1-C_3$alkyl or $C_1-C_3$alkoxy, it being possible for the last two groups mentioned to be substituted by halogen or mono-substituted by $C_1-C_3$alkoxy, Y is hydrogen, $C_1-C_3$alkyl, $C_1-C_3$alkoxy or $C_1-C_3$alkylthio, it being possible for the last three groups mentioned to be substituted by halogen or mono- or di-substituted by $C_1-C_3$alkoxy or by $C_1-C_3$alkylthio, or Y is a group of the formula $NR_{10}R_{11}$, $C_3-C_6$cycloalkyl, $C_2-C_4$alkenyl, $C_2-C_4$alkynyl, $C_3$- or $C_4$-alkenyloxy or $C_3$- or $C_4$-alkynyloxy, Z is CH or N, $R_{10}$ and $R_{11}$ are each independently of the other hydrogen, $C_1-C_3$alkyl or $C_3$- or $C_4$-alkenyl, $X_1$ is $CH_3$, $OCH_3$, $OC_2H_5$ or $OCF_2H$, $Y_1$ is $-O-$ or $-CH_2-$, $X_2$ is $CH_3$, $C_2H_5$ or $CH_2CF_3$, $Y_2$ is $OCH_3$, $OC_2H_5$, $SCH_3$, $SC_2H_5$, $CH_3$ or $C_2H_5$, $X_3$ is $CH_3$ or $OCH_3$, $Y_3$ is hydrogen or $CH_3$, $X_4$ is $CH_3$, $OCH_3$, $OC_2H_5$, $CH_2OCH_3$ or chlorine, $Y_4$ is $CH_3$, $OCH_3$, $OC_2H_5$ or chlorine and $Y_5$ is $CH_3$, $C_2H_5$, $OCH_3$ or chlorine, or an N-oxide or a salt of a compound of formula I, and b) a herbicide-antagonistically effective amount of a sulfamoylphenylurea of formula II

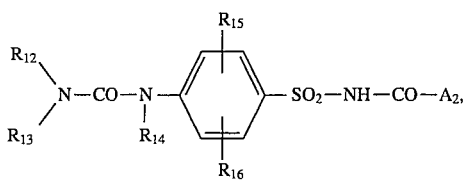

(II)

wherein

A$_2$ is a group

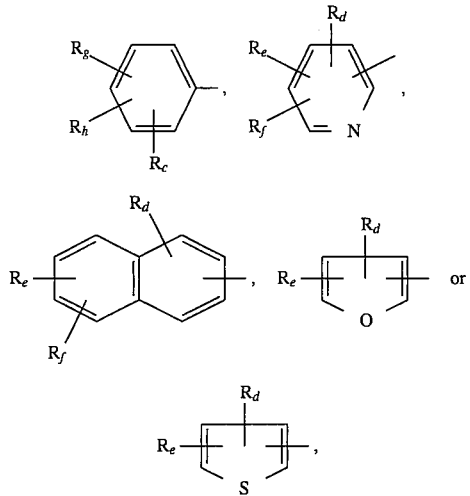

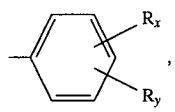

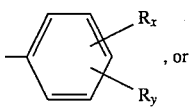 or $R_{12}$ and $R_{13}$ are each independently of the other hydrogen, $C_1$–$C_8$alkyl, $C_3$–$C_8$cycloalkyl, $C_3$–$C_6$alkenyl, $C_3$–$C_6$alkynyl, —⟨phenyl⟩—$R_x$, $R_y$ or $C_1$–$C_4$alkyl substituted by $C_1$–$C_4$alkoxy or by —⟨phenyl⟩—$R_x$, $R_y$, or $R_{12}$ and $R_{13}$ together are a $C_4$–$C_6$alkylene bridge or a $C_4$–$C_6$alkylene bridge interrupted by oxygen, sulfur, SO, SO$_2$, NH or by —N($C_1$–$C_4$alkyl)—, $R_{14}$ is hydrogen or $C_1$–$C_4$alkyl, $R_{15}$ and $R_{16}$ are each independently of the other hydrogen, halogen, cyano, nitro, trifluoromethyl, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$, CONR$_k$R$_m$, —COR$_n$, —SO$_2$NR$_k$R$_m$ or —OSO$_2$—$C_1$–$C_4$ alkyl, or $R_{15}$ and $R_{16}$ together are a $C_3$- or $C_4$-alkylene bridge that may be substituted by halogen or by $C_1$–$C_4$alkyl, or a $C_3$–$C_4$alkenylene bridge that may be substituted by halogen or by $C_3$- or $C_4$-alkyl, or a butadienylene bridge that may be substituted by halogen or by $C_1$–$C_4$alkyl, and $R_g$ and $R_h$ are each independently of the other hydrogen, halogen, $C_1$–$C_4$alkyl, trifluoromethyl, methoxy, methylthio or —COOR$_j$, wherein $R_c$ is hydrogen, halogen, $C_1$–$C_4$alkyl or methoxy, $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$ or —CONR$_k$R$_m$, $R_e$ is hydrogen, halogen, $C_1$–$C_4$halogen, $C_1$–$C_4$alkyl, —COOR$_j$, trifluoromethyl or methoxy, or $R_d$ and $R_e$ together are a $C_3$–$C_4$alkylene bridge, $R_f$ is hydrogen, halogen or $C_1$–$C_4$alkyl, $R_x$ and $R_y$ are each independently of the other hydrogen, halogen, $C_1$–$C_4$alkyl, $C_1$–$C_4$alkoxy, $C_1$–$C_4$alkylthio, —COOR$_{17}$, trifluoromethyl, nitro or cyano, $R_j$, $R_k$ and $R_m$ are each independently of the other hydrogen or $C_1$–$C_4$alkyl, $R_k$ and $R_m$ together are a $C_4$–$C_6$alkylene bridge or a $C_4$–$C_6$alkylene bridge interrupted by oxygen, NH or by —N($C_1$–$C_4$alkyl)—;

$R_{17}$ is hydrogen, $C_1$–$C_{10}$alkyl, $C_1$–$C_4$alkoxy-$C_1$–$C_4$alkyl, $C_1$–$C_4$ alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$cycloalkyl, halo-$C_3$–$C_7$cycloalkyl, $C_1$–$C_8$alkylcarbonyl, allylcarbonyl, $C_3$–$C_7$cycloalkylcarbonyl, benzoyl that is unsubstituted or substituted at the phenyl ring by up to three identical or different substituents selected from halogen, $C_1$–$C_4$alkyl, halo-$C_1$–$C_4$alkyl, halo-$C_1$–$C_4$alkoxy and $C_1$–$C_4$ alkoxy; or is furoyl, thienyl; or $C_1$–$C_4$alkyl substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$ alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$alkylaminocarbonyl; or phenylaminocarbonyl that is unsubstituted or substituted at the phenyl by up to three identical or different substituents selected from halogen, $C_1$–$C_4$alkyl, halo-$C_1$–$C_4$alkyl, halo-$C_1$–$C_4$alkoxy and $C_1$–$C_4$ alkoxy or mono-substituted by cyano or by nitro, or is dioxolan-2-yl that is unsubstituted or substituted by one or two $C_1$–$C_4$alkyl groups, or dioxan-2-yl that is unsubstituted or substituted by one or two $C_1$–$C_4$alkyl groups, or $C_1$–$C_4$alkyl substituted by cyano, nitro, carboxy or by $C_1$–$C_8$alkylthio-$C_1$–$C_8$alkoxycarbonyl, and $R_n$ is $C_1$–$C_4$alkyl, phenyl, or phenyl substituted by halogen, $C_1$–$C_4$alkyl, methoxy, nitro or by trifluoromethyl, or a salt of a compound of formula II.

The present invention relates also to the use of the composition according to the invention in the control of weeds and grasses in crops of useful plants, especially maize.

In the definitions of the compounds of formulae I and II, halogen is to be understood as being fluorine, chlorine, bromine and iodine, but preferably fluorine, chlorine and bromine, especially chlorine. Alkyl is to be understood as being straight-chained or branched alkyl, for example methyl, ethyl, n-propyl, isopropyl or the four butyl isomers. Longer-chained alkyl groups include the isomers of pentyl, hexyl, heptyl and octyl, the unbranched chains being preferred in each case. Alkoxy is to be understood as being: methoxy, ethoxy, n-propoxy, isopropoxy or the four butoxy isomers, but especially methoxy, ethoxy or isopropoxy. Alkyl substituted by alkoxy is preferably methoxymethyl, ethoxymethyl, methoxyethyl and ethoxyethyl, but especially methoxyethyl. Alkyl substituted by unsubstituted or substituted phenyl is preferably a derivative of phenylethyl or benzyl. Typical alkenyl and alkynyl groups are allyl, 2-butenyl, methallyl, 3-butenyl, propargyl, 2-butynyl, 3-butynyl and 2-pentenyl. Examples of cycloalkyl are cyclopropyl, cyclopentyl, cyclohexyl and cycloheptyl, but preferably cyclopentyl and cyclohexyl. Heterocycles are, for example, pyrrolidine, piperidine, pyrazolidine, imidazolidine, oxazolidine, thiazolidine, morpholine, thiomorpholine, piperazine or hexahydroazepine and in the case of sulfur-containing rings the oxidation products thereof. Alkyl in alkylthio, alkylsulfinyl or alkylsulfonyl has the specific meanings listed above.

When substituents together form a $C_3$–$C_4$alkylene bridge, a $C_3$–$C_4$alkenylene bridge or a butadienylene bridge, each of which may be substituted by halogen or by $C_1$–$C_4$alkyl, there are formed, for example together with a phenyl ring to which the bridge is bonded, binuclear systems, such as 1,2,3,4-tetrahydronaphthalene, 1-chloro-2-methyl-3,4-dihydronaphthalene, indane, 1,2-dihydronaphthalene, indene, naphthalene, 2-methylnaphthalene, 1-n-butylnaphthalene, 2-ethylnaphthalene or 1-chloronaphthalene.

When substituents together form a $C_3$- or $C_4$-alkylene bridge, there are formed, together with the ring system to which they are bonded, polynuclear systems, such as 2,3-tetramethylenethiophene, 2,3-trimethylenethiophene, 2,3-tetramethylenefuran, 3,4-tetramethylenepyridine or

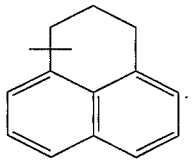

N-Oxides of a compound of formula I are to be understood as being compounds containing a group of the formula

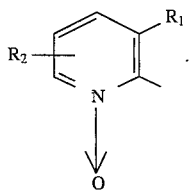

The invention relates also to salts that the compounds of formulae I and II are capable of forming with amines, alkali metal and alkaline earth metal bases or quaternary ammonium bases. Salt formation can also be effected by the addition of a strong acid to the pyrimidine moiety of a compound of formula I. Suitable acids for that purpose are hydrochloric acid, hydrobromic acid, sulfuric acid or nitric acid.

Alkali metal and alkaline earth metal hydroxides that are especially suitable as salt formers are the hydroxides of lithium, sodium, potassium, magnesium or calcium, but especially those of sodium or potassium.

Examples of amines suitable for the formation of ammonium cations are both ammonia and primary, secondary and tertiary $C_1$–$C_4$alkylamines, $C_1$–$C_4$-hydroxyalkylamines and $C_2$–$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methylhexylamine, methyl-nonylamine, methyl-pentadecylamine, methyl-octadecylamine, ethyl-butylamine, ethyl-heptylamine, ethyl-octylamine, hexyl-heptylamine, hexyl-octylmine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, diethanolamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, such as pyridine, quinoline, isoquinoline, morpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

Examples of quaternary ammonium bases are generally the cations of ammonium halides, for example the tetramethylammonium cation, the trimethylbenzylammonium cation, the triethylbenzylammonium cation, the tetraethylammonium cation, the trimethylethylammonium cation, and also the ammonium cation.

Compounds of formula I that are preferred for use in a composition according to the invention are those wherein $R_1$ is —$NR_6R_7$, and especially those wherein $R_6$ is $C_1$–$C_4$alkyl and $R_7$ is $C_1$–$C_4$alkylsulfonyl.

Also preferred are compounds wherein $R_2$ is hydrogen.

Compounds wherein $R_3$ is hydrogen are also suitable.

A group of especially preferred compounds comprises those wherein $A_1$ is a group of the formula

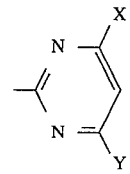

wherein

X and Y are each independently of the other hydrogen, $C_1$–$C_3$alkyl or $C_1$–$C_3$alkoxy.

Compounds of formula II preferred for use in a composition according to the invention are those wherein $A_2$ is a group of the formula

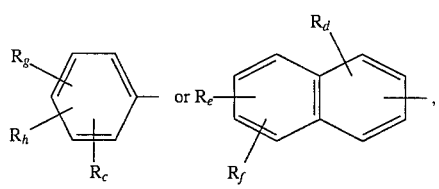

wherein $R_g$ and $R_h$ are each independently of the other hydrogen, halogen, $C_1$–$C_4$alkyl, trifluoromethyl, methoxy, methylthio or $COOR_j$, wherein $R_c$ is hydrogen, halogen, $C_1$–$C_4$alkyl or methoxy, $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —$COOR_j$ or —$CONR_kR_m$, $R_e$ is hydrogen, halogen, $C_1$–$C_4$alkyl, —$COOR_j$, trifluoromethyl or methoxy, or $R_d$ and $R_c$ together form a $C_3$- or $C_4$-alkylene bridge, $R_f$ is hydrogen, halogen or $C_1$–$C_4$alkyl, $R_j$, $R_k$ and $R_m$ are each independently of the other hydrogen or $C_1$–$C_4$alkyl, and $R_k$ and $R_m$ together are a $C_4$–$C_6$alkylene bridge or a $C_4$–$C_6$alkylene bridge interrupted by oxygen, NH or by —N($C_1$–$C_4$alkyl)—.

Of those compounds preference is given especially to those wherein $R_c$, $R_d$, $R_e$, $R_g$ and $R_h$ are each independently of the others hydrogen, $C_1$–$C_4$alkyl or methoxy.

Other especially suitable groups of compounds of formula II are those wherein $R_{15}$ and $R_{16}$ are hydrogen; or $R_{13}$ and $R_{14}$ are hydrogen; or the sulfamoyl group occupies the 4-position of the phenyl ring.

Also suitable are those compounds of formula II wherein $R_{13}$, $R_{14}$ and $R_{15}$ are hydrogen and the sulfamoyl group occupies the 4-position of the phenyl ring.

Especially valuable compositions according to the present invention are those comprising The pyridylsulfonylureas of formula I used according to the invention and the preparation thereof are described, for example, in DE-A-40 00 503. The sulfamoylphenylureas of formula II used for the compositions according to the invention and the preparation thereof are known, for example, from EP-A-365 484.

The invention relates also to a method for the selective control of weeds in crops of useful plants, which method comprises treating the useful plants, the seed, such as the seeds or cuttings, thereof or the cultivated area thereof with a herbicidally effective amount of a pyridylsulfonylurea of formula I and a herbicide-antagonistically effective amount of a sulfamoylphenylurea of formula II, simultaneously or independently of one another.

Crop plants that can be protected against the damaging effect of the above-mentioned herbicides of formula I are especially those that are important in the food or textile sectors, for example sugar cane and, especially, sorghum and

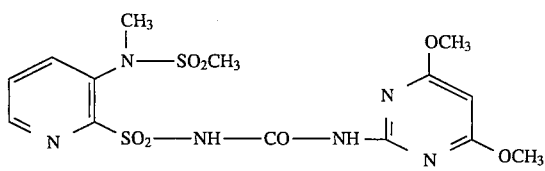

and as compound of formula II a compound of formula IIa

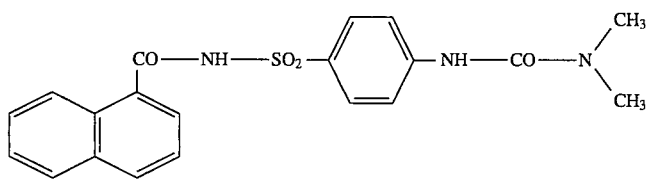

or of formula IIb

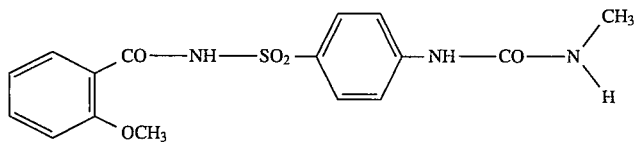

or of formula IIc

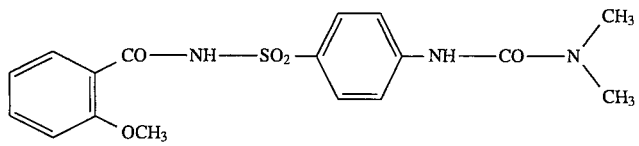

or of formula IId

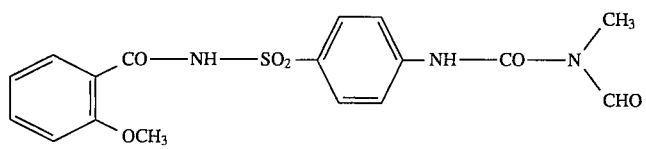

or of formula IIe

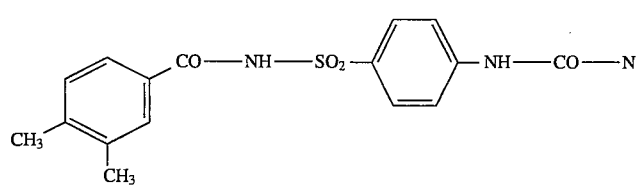

maize, as well as rice and other species of cereal, such as wheat, rye, barley and oats.

The weeds to be controlled may be both monocotyledonous and dicotyledonous weeds.

There come into consideration as crop plants or parts of those plants, for example, those mentioned above. Cultivated areas will be understood as meaning areas of land in which the crop plants are already growing or in which the seed of those crop plants has already been sown, and also ground intended for growing those crop plants.

A safener or antidote of formula II can, depending on the intended use, be used to pre-treat the seed of the crop plant (dressing the seeds or cuttings) or can be introduced into the soil before or after sowing has taken place. It can, however, also be applied by itself or together with the herbicide before or after the emergence of the plants. The treatment of the plant or the seed with the safener can therefore in principle take place independently of the time of application of the phytotoxic chemical. The plant can, however, also be treated by applying the phytotoxic chemical and the safener simultaneously (tank mixture). Preemergence treatment includes both treatment of the cultivated area before sowing and treatment of cultivated areas in which seed has been sown but in which the plants have not yet grown.

The rate of application of the safener relative to that of the herbicide depends largely on the mode of application. In the case of field treatment, which is effected either using a tank mixture with a combination of safener and herbicide or by separate application of safener and herbicide, the ratio of safener to herbicide is generally from 1:100 to 1:1, preferably from 1:20 to 1:1, and especially 1:1. In contrast, in the case of seed dressing, much lower amounts of safener are required relative to the rate of application of herbicide per hectare of cultivated area.

In the case of field treatment, 0.001 to 5.0 kg of safener/ha, preferably 0.005 to 0.5 kg of safener/ha, will usually be applied.

The rate of application of herbicide is generally from 0.001 to 2 kg/ha, but preferably from 0.001 to 0.5 kg/ha.

In the case of seed-dressing, 0.001 to 10 g of safener/kg of seed, preferably 0.05 to 2 g of safener/kg of seed, will generally be applied. If the safener is applied in liquid form by seed soaking shortly before sowing, then it is advantageous to use safener solutions that comprise the active ingredient in a concentration of 1 to 10 000 ppm, preferably 100 to 1000 ppm.

For the purpose of application, the compounds of formula II or combinations of compounds of formula II with the herbicides to be antagonised are advantageously used together with the adjuvants conventionally employed in formulation technology, and are therefore formulated in known manner, e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions to be used, the methods of application, such as spraying, atomising, dusting, scattering, coating or pouring, are chosen in accordance with the intended objectives and the prevailing circumstances.

The formulations, i.e. the compositions, preparations or mixtures comprising the compound (active ingredient) of formula II, or a combination of the compound of formula II with the herbicide of formula I to be antagonised, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the compound of formula II to be formulated and, where appropriate, also on the nature of the herbicide of formula I to be antagonised, suitable surface-active compounds are nonionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Fatty acid methyltaurin salts may also be mentioned.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl groups, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxy-polyethoxyethanol.

Fatty acid esters of polyoxyethylene sorbitan, e.g. polyoxyethylene sorbitan trioleate, are also suitable.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl groups. The salts are preferably in the form of halides, methyl sulfates or ethyl sulfates, e.g. stearyltrimethyl-ammonium chloride or benzyldi(2-chloroethyl)ethylammonium bromide.

The surfactants customarily employed in formulation technology are described inter alia in the following publications:

"Mc Cutcheon's Detergents and Emulsifiers Annual" MC Publishing Corp., Ridgewood, N.J., 1981.

Stache, H., "Tensid-Taschenbuch", Carl Hanser Verlag, Munich/Vienna 1981.

The agrochemical compositions usually comprise 0.1 to 99% by weight, preferably 0.1 to 95% by weight, of a compound of formula II or a mixture of antidote and herbicide, 1 to 99.9% by weight, preferably 5 to 99.8% by weight, of a solid or liquid adjuvant and 0 to 25% by weight, preferably 0.1 to 25% by weight, of a surfactant.

Whereas commercial products are preferably formulated as concentrates, the end user will normally employ dilute formulations.

The compositions may also comprise further ingredients such as stabilisers, antifoams, viscosity regulators, binders and tackifiers, as well as fertilisers or other active ingredients for obtaining special effects.

Various methods and techniques are suitable for using compounds of formula II or compositions comprising them for protecting crop plants against the damaging effects of herbicides of formula I. The following are examples thereof:

i) Seed Dressing a) Dressing the seeds with a wettable powder formulation of a compound of formula II by shaking in a vessel until the formulation is evenly distributed over the surface of the seeds (dry dressing). Approximately 1 to 500 g of a compound of formula II (4 g to 2 kg of wettable powder) are used per 100 kg of seed.

b) Dressing the seeds with an emulsifiable concentrate of a compound of formula II according to method a) (wet dressing).

c) Dressing by immersing the seeds in a mixture comprising 100 to 1000 ppm of a compound of formula II for 1 to 72 hours and, if desired, subsequently drying the seeds (immersion dressing).

Dressing the seed or treating the germinated seedling are naturally the preferred methods of application since the active ingredient treatment is directed wholly at the target crop. Normally 1 to 1000 g of antidote, preferably 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application from a Tank Mixture

A liquid formulation of a mixture of antidote and herbicide (ratio of the one to the other from 10:1 to 1:100) is used, the rate of application of herbicide being 0.01 to 5.0 kg per hectare. A tank mixture of this type is applied before or after sowing.

iii) Application to the Seed Furrow

The antidote is introduced in the form of an emulsifiable concentrate, wettable powder or granules into the open, sown seed furrow and then, after the seed furrow has been covered, the herbicide is applied preemergence in the normal manner.

iv) Controlled Release of Active Ingredient

A solution of a compound of formula II is applied to mineral granule carriers or polymerised granules (urea/formaldehyde) and allowed to dry. If desired, a coating may be applied (coated granules) that allows the active ingredient to be released in metered amounts over a specific period of time.

The action of the compositions according to the invention is illustrated in detail by the following Examples.

Formulation Examples for active ingredients of formula II or mixtures thereof with a herbicide of formula I (throughout, percentages are by weight)

| 1. Emulsifiable concentrates | a) | b) | c) |
|---|---|---|---|
| compound mixture | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2. Solutions | a) | b) | c) | d) |
|---|---|---|---|---|
| compound mixture | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190°) | — | — | 94% | — |

These solutions are suitable for application in the form of micro-drops.

| 3. Granules | a) | b) |
|---|---|---|
| compound mixture | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | a) | b) |
|---|---|---|
| compound mixture | 2% | 5% |
| highly dispersed silicic acid | 1% | 5% |

| 4. Dusts | a) | b) |
|---|---|---|
| talcum | 97% | — |
| kaolin | — | 90% |

Ready-for-use dusts are obtained by intimately mixing the carriers with the active ingredient.

| 5. Wettable powders | a) | b) | c) |
|---|---|---|---|
| compound mixture | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrates | |
|---|---|
| compound mixture | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration can be obtained from this concentrate by dilution with water.

| 7. Dusts | a) | b) |
|---|---|---|
| compound mixture | 5% | 8% |
| talcum | 95% | — |
| kaolin | — | 92% |

Ready-for-use dusts are obtained by mixing the active ingredient with the carrier and grinding the mixture in a suitable mill.

| 8. Extruder granules | |
|---|---|
| compound mixture | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 9. Coated granules | |
|---|---|
| compound mixture | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 10. Suspension concentrates | |
|---|---|
| compound mixture | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE B1

Postemergence Phytotoxic Action of the Herbicides of Formula I and of the Mixtures of Herbicide and Safener of Formula II on Maize Under greenhouse conditions maize is grown in plastics pots to the 2.5-leaf stage. At that stage, a herbicide by itself and a mixture of the herbicide and safeners are applied to the test plants. The test compounds are applied in the form of an aqueous suspension in 500 l of water/ha. The rates of application for the herbicide are 125/60/30/15 g/ha and the rate of application for the safeners is 60 g/ha. 21 days after application the test is evaluated according to a scale of percentages. 100% denotes that the test plant has died, 0% denotes no phytotoxic action. The results shown in Table 1 are obtained. The results show that the safeners used clearly reduce the damage to maize caused by the herbicide.

TABLE 1

| Herbicide | Safener, g/ha | Herbicide concentration g/ha | | | | |
|---|---|---|---|---|---|---|
| | | 125 | 60 | 30 | 15 | 8 |
| Ia | — | 85 | 70 | 60 | 50 | 30 |
| Ia | IIa, 60 | 40 | 30 | 25 | 10 | 0 |
| Ia | IIb, 60 | 15 | 0 | 0 | 0 | 0 |
| Ia | IIc, 60 | 20 | 0 | 0 | 0 | 0 |
| Ia | IId, 60 | 0 | 0 | 0 | 0 | 0 |

EXAMPLE B2

Use of a Mixture of Herbicide of Formula I and Safener of Formula II for Seed Dressing in Maize Maize seed is dressed with a safener in a concentration corresponding to 1 g/kg of seed. The maize is then grown on under greenhouse conditions in plastics pots to the 2.5-leaf stage. Untreated maize is grown in parallel with the treated maize to the same stage. At that stage, the herbicide is applied to the treated and the untreated test plants. The herbicide is applied in the form of an aqueous suspension in 500 l of water/ha. The rate of application for the herbicide is 125, 60, 30 g/ha and the rate of application for the seed-dressing safener is 1 g/kg of seed. 14 days after application the test is evaluated according to a scale of percentages. 100% denotes that the test plant has died, 0% denotes no phytotoxic action. The results shown in Table 2 are obtained. The results show that the safener in the form of a seed-dressing formulation clearly reduces the damage caused post-emergence by the herbicide. Similar results are obtained when the herbicide is applied preemergence.

TABLE 2

| Herbicide | Safener, g/ha | 125 | 60 | 30 |
|---|---|---|---|---|
| Ia | — | 90 | 70 | 50 |
| Ia | IIa, 1 | 10 | 0 | 0 |

What is claimed is:

1. A composition for the selective control of weeds in crops of useful plants, which comprises as active component, in addition to inert carriers and additives, a mixture comprising a) a herbicidally effective amount of a pyridylsulfonylurea of formula I

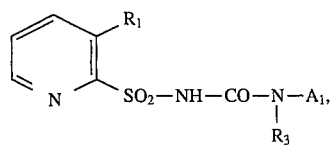

wherein $R_1$ is $-NR_6R_7$, $R_3$ is hydrogen, $R_6$ is $C_1-C_4$alkyl $R_7$ is $C_1-C_4$alkylsulfonyl $A_1$ is a group of the formula

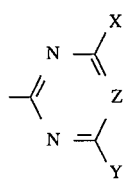

X is $C_1-C_3$alkyl or $C_1-C_3$alkoxy

Y is $C_1-C_3$alkyl or $C_1-C_3$alkoxy

Z is CH or N, and b) a herbicide-antagonistically effective amount of a sulfamoylphenylurea of formulae II or IId

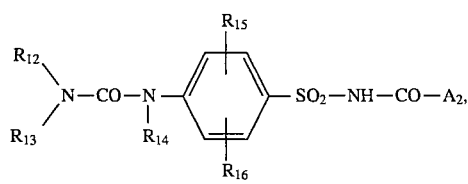

wherein $A_2$ is a group

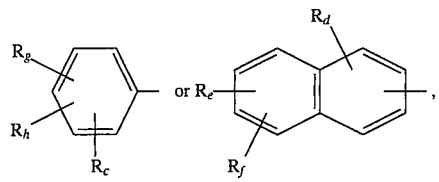

$R_{12}$ and $R_{13}$ are each independently of the other hydrogen or $C_1-C_8$alkyl, $R_{14}$ is hydrogen $R_{15}$ and $R_{16}$ are each hydrogen and $R_g$ and $R_h$ are each independently of the other hydrogen or $C_1-C_4$alkyl wherein $R_c$ is hydrogen or methoxy, $R_d$ is hydrogen $R_e$ is hydrogen $R_f$ is hydrogen or a salt of a compound of formulae II or IId.

2. A composition according to claim 1 wherein in a compound of formula I $A_1$ is a group of the formula

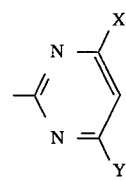

wherein

X and Y are each independently of the other $C_1-C_3$alkyl or $C_1-C_3$alkoxy.

3. A composition according to claim 1 wherein in a compound of formula II $R_{13}$ is hydrogen.

4. A composition according to claim 1 comprising as

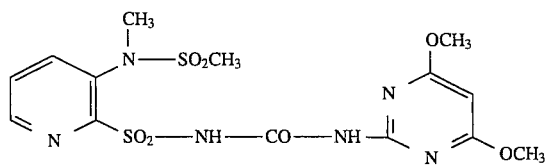

and as compound of formula II a compound of formula IIa

-continued

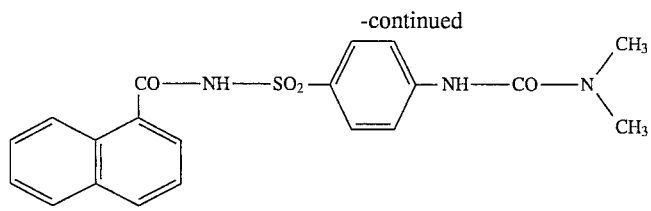

or of formula IIb

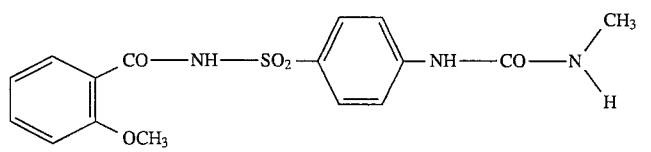

or of formula IIc

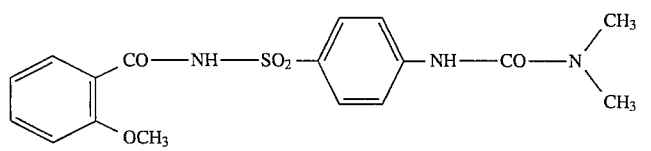

or of formula IId

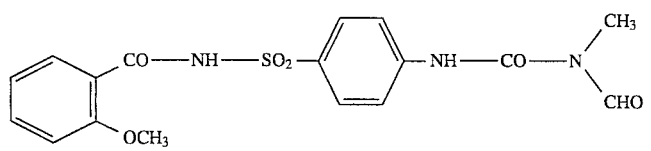

or of formula IIe

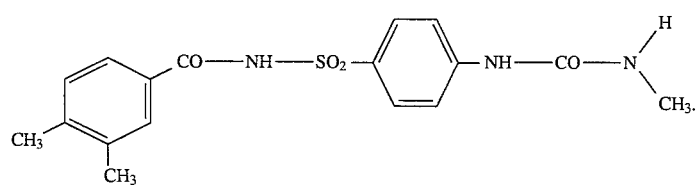

5. A method for the selective control of weeds and grasses in crops of useful plants, which comprises treating the crops, the seed thereof or the cultivated area thereof with an effective amount of a herbicide of formula I

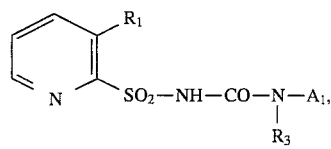

wherein
$R_1$ is —$NR_6R_7$,
$R_3$ is hydrogen,
$R_6$ is $C_1$-$C_4$alkyl
$R_7$ is $C_1$-$C_4$alkylsulfonyl
$A_1$ is a group of the formula

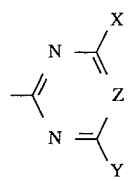

$X$ is $C_1$-$C_3$alkyl or $C_1$-$C_3$alkoxy
$Y$ is $C_1$-$C_3$alkyl or $C_1$-$C_3$alkoxy
$Z$ is CH or N, and
a herbicide-antagonistically effective amount of a compound of formula II or IId,

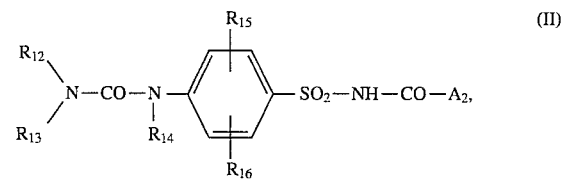

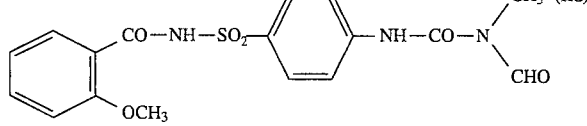

wherein $A_2$ is a group

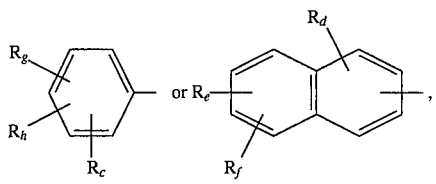

$R_{12}$ and $R_{13}$ are each independently of the other hydrogen or $C_1$–$C_8$alkyl, $R_{14}$ is hydrogen $R_{15}$ and $R_{16}$ are each hydrogen and $R_g$ and $R_h$ are each independently of the other hydrogen or $C_1$–$C_4$alkyl wherein $R_c$ is hydrogen or methoxy, $R_d$ is hydrogen $R_e$ is hydrogen $R_f$ is hydrogen or a salt of a compound of formulae II or IId,
wherein said herbicidal compounds I and safeners II or IId are applied simultaneously or independently of one another.

6. A method according to claim 5, which comprises treating crop plants or cultivated areas intended for crop plants with 0.001 to 2 kg/ha of a compound of formula I and an amount of 0.005 to 0.5 kg/ha of a compound of formula II or IId.

7. A method according to claim 5 for the selective control of weeds and grasses in maize crops.

* * * * *